(12) United States Patent
Moskowitz et al.

(10) Patent No.: US 11,491,021 B2
(45) Date of Patent: *Nov. 8, 2022

(54) ELECTRONICALLY ASSISTED MEDICAL DEVICE (71) Applicant: Moskowitz Family LLC, Rockville, MD (US)

(72) Inventors: Mosheh T. Moskowitz, Rockville, MD (US); Nathan C. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/208,669

(22) Filed: Mar. 22, 2021

(65) Prior Publication Data
US 2021/0315708 A1 Oct. 14, 2021

Related U.S. Application Data (60) Continuation of application No. 16/134,364, filed on Sep. 18, 2018, now Pat. No. 10,952,867, which is a
(Continued)

(51) Int. Cl.
A61F 2/44 (2006.01)
A61B 17/68 (2006.01)
(Continued)

(52) U.S. Cl.
CPC ............ A61F 2/4425 (2013.01); A61B 17/60 (2013.01); A61B 17/66 (2013.01); A61B 17/68 (2013.01);
(Continued)

(58) Field of Classification Search
CPC ... A61B 17/60; A61B 2017/603; A61B 17/62; A61B 17/66; A61B 17/68;
(Continued)

(56) References Cited

U.S. PATENT DOCUMENTS 4,954,952 A 9/1990 Ubhayakar et al.
5,720,746 A 2/1998 Soubeiran
(Continued)

FOREIGN PATENT DOCUMENTS

FR 2727003 5/1996

OTHER PUBLICATIONS

Feipel, et al., "Three-dimensional kinematics of the lumbar spine during treadmill walking at different speeds," Eur. Spine J., 2001, 10:16-22.
(Continued)

Primary Examiner — Larry E Waggle, Jr.
(74) Attorney, Agent, or Firm — Fish & Richardson P.C.

(57) ABSTRACT

An electronically assisted artificial vertebral disc having an upper disc plate and a lower disc plate is disclosed. An actuator imparts movement to at least one of the upper and lower disc plates. A control device controls the actuator and the amount of movement between the disc plates. The actuator includes a plurality of either linear actuators or rotary actuators that are driven by electric motors in response to the control device. The control device includes at least a first sensor for detecting the position of the actuator and at least a second sensor for detecting the spatial orientation of at least one of the upper and lower disc plates. The control device also preferably includes a microprocessor that calculates the desired positions of the upper and lower disc plates and provides a control signal to the actuator to drive the upper and lower disc plates to their desired positions.

8 Claims, 12 Drawing Sheets

Related U.S. Application Data continuation of application No. 15/350,352, filed on Nov. 14, 2016, now Pat. No. 10,123,881, which is a continuation of application No. 12/945,835, filed on Nov. 13, 2010, now Pat. No. 9,492,282, which is a division of application No. 11/737,846, filed on Apr. 20, 2007, now Pat. No. 7,854,765.

(60) Provisional application No. 60/793,329, filed on Apr. 20, 2006.

(51) Int. Cl.
  A61B 17/66 (2006.01)
  A61B 17/60 (2006.01)
  A61B 17/88 (2006.01)
  A61B 17/70 (2006.01)
  A61F 2/30 (2006.01)
  A61F 2/46 (2006.01)
  A61F 2/48 (2006.01)

(52) U.S. Cl.
  CPC .............. A61B 17/70 (2013.01); A61B 17/88 (2013.01); A61B 17/885 (2013.01); A61F 2/44 (2013.01); A61F 2/442 (2013.01); A61B 2017/681 (2013.01); A61F 2/48 (2021.08); A61F 2002/30079 (2013.01); A61F 2002/30242 (2013.01); A61F 2002/30523 (2013.01); A61F 2002/30538 (2013.01); A61F 2002/30579 (2013.01); A61F 2002/30841 (2013.01); A61F 2002/30904 (2013.01); A61F 2002/443 (2013.01); A61F 2002/4632 (2013.01); A61F 2002/4667 (2013.01); A61F 2210/009 (2013.01); A61F 2220/0025 (2013.01); A61F 2230/0071 (2013.01); A61F 2250/0006 (2013.01)

(58) Field of Classification Search
  CPC ... A61B 2017/681; A61B 17/70; A61B 17/88; A61B 17/885; A61F 2002/30523; A61F 2002/30538; A61F 2/44; A61F 2/442; A61F 2/4425; A61F 2002/443; A61F 2002/48
  See application file for complete search history.

(56) References Cited

U.S. PATENT DOCUMENTS

| | | | |
|---|---|---|---|
| 5,827,328 A * | 10/1998 | Buttermann | A61F 2/442 623/17.13 |
| 6,063,121 A * | 5/2000 | Xavier | A61F 2/4425 606/907 |
| 6,224,602 B1 | 5/2001 | Hayes | |
| 6,235,034 B1 | 5/2001 | Bray | |
| 6,322,562 B1 | 11/2001 | Wolter | |
| 6,342,074 B1 | 1/2002 | Simpson | |
| 6,375,682 B1 | 4/2002 | Fleischmann et al. | |
| 6,385,509 B2 | 5/2002 | Das et al. | |
| 6,454,807 B1 | 9/2002 | Jackson | |
| 6,519,860 B1 | 2/2003 | Bieg et al. | |
| 6,629,998 B1 | 10/2003 | Lin | |
| 6,706,042 B2 | 3/2004 | Taylor | |
| 6,716,247 B2 | 4/2004 | Michelson | |
| 6,890,355 B2 | 5/2005 | Michelson | |
| 7,115,144 B2 | 10/2006 | Diaz et al. | |
| 7,118,601 B2 * | 10/2006 | Yasui | A61F 2/60 403/56 |
| 7,211,112 B2 | 5/2007 | Baynham et al. | |
| 7,232,464 B2 | 6/2007 | Mathieu et al. | |
| 7,238,203 B2 | 7/2007 | Bagga et al. | |
| 7,442,209 B2 | 10/2008 | Michelson | |
| 7,445,605 B2 | 11/2008 | Overall | |
| 7,531,002 B2 | 5/2009 | Sutton et al. | |
| 7,531,006 B2 * | 5/2009 | Clausen | A61F 2/66 623/53 |
| 7,776,047 B2 | 8/2010 | Fanger et al. | |
| 7,854,765 B2 * | 12/2010 | Moskowitz | A61B 17/70 623/17.14 |
| 8,268,000 B2 | 9/2012 | Waugh et al. | |
| 8,333,766 B2 | 12/2012 | Edelhauser | |
| 9,155,544 B2 | 10/2015 | Bonutti | |
| 9,492,282 B2 * | 11/2016 | Moskowitz | A61B 17/60 |
| 10,123,881 B2 * | 11/2018 | Moskowitz | A61B 17/88 |
| 2002/0010465 A1 * | 1/2002 | Koo | A61B 17/62 606/57 |
| 2003/0163206 A1 | 8/2003 | Yasui et al. | |
| 2004/0177531 A1 | 9/2004 | DiBenedetto et al. | |
| 2004/0186569 A1 | 9/2004 | Berry | |
| 2005/0234555 A1 * | 10/2005 | Sutton | A61F 2/4425 623/18.12 |
| 2005/0256576 A1 | 11/2005 | Moskowitz et al. | |
| 2005/0261769 A1 | 11/2005 | Moskowitz et al. | |
| 2005/0273170 A1 | 12/2005 | Navarro et al. | |
| 2006/0004447 A1 | 1/2006 | Mastrorio et al. | |
| 2006/0069447 A1 | 3/2006 | DiSilvestro et al. | |
| 2006/0241621 A1 | 10/2006 | Moskowitz et al. | |
| 2007/0049943 A1 | 3/2007 | Moskowitz et al. | |
| 2007/0156157 A1 | 7/2007 | Nahum et al. | |
| 2007/0167678 A1 | 7/2007 | Moskowitz et al. | |
| 2007/0198089 A1 | 8/2007 | Moskowitz et al. | |
| 2007/0250172 A1 | 10/2007 | Moskowitz et al. | |
| 2008/0033440 A1 | 2/2008 | Moskowitz et al. | |
| 2008/0177307 A1 | 7/2008 | Moskowitz et al. | |
| 2008/0281424 A1 | 11/2008 | Parry et al. | |
| 2009/0105831 A1 | 4/2009 | Jones et al. | |
| 2009/0112271 A1 | 4/2009 | Moskowitz et al. | |
| 2009/0224023 A1 | 9/2009 | Moskowitz et al. | |
| 2009/0234455 A1 | 9/2009 | Moskowitz et al. | |
| 2010/0145460 A1 | 6/2010 | McDonough et al. | |
| 2010/0324606 A1 | 12/2010 | Moskowitz et al. | |
| 2011/0125269 A1 | 5/2011 | Moskowitz et al. | |
| 2011/0137349 A1 | 6/2011 | Moskowitz et al. | |
| 2011/0160861 A1 | 6/2011 | Jimenez | |
| 2011/0178600 A1 | 7/2011 | Moskowitz et al. | |
| 2011/0208312 A1 | 8/2011 | Moskowitz et al. | |
| 2011/0288646 A1 | 11/2011 | Moskowitz et al. | |
| 2011/0295327 A1 | 12/2011 | Moskowitz et al. | |
| 2011/0295371 A1 | 12/2011 | Moskowitz et al. | |
| 2011/0307011 A1 | 12/2011 | Moskowitz et al. | |
| 2011/0319935 A1 | 12/2011 | Moskowitz et al. | |
| 2012/0010714 A1 | 1/2012 | Moskowitz et al. | |
| 2012/0330419 A1 | 12/2012 | Moskowitz et al. | |
| 2013/0018468 A1 | 1/2013 | Moskowitz et al. | |
| 2013/0018469 A1 | 1/2013 | Moskowitz et al. | |
| 2013/0018470 A1 | 1/2013 | Moskowitz et al. | |
| 2013/0023991 A1 | 1/2013 | Moskowitz et al. | |
| 2013/0023992 A1 | 1/2013 | Moskowitz et al. | |
| 2013/0053962 A1 | 2/2013 | Moskowitz et al. | |
| 2013/0173002 A1 | 7/2013 | Moskowitz et al. | |
| 2013/0282017 A1 | 10/2013 | Moskowitz et al. | |
| 2014/0249629 A1 | 9/2014 | Moskowitz et al. | |
| 2015/0025637 A1 | 1/2015 | Moskowitz et al. | |
| 2015/0105824 A1 | 4/2015 | Moskowitz et al. | |
| 2015/0148847 A1 | 5/2015 | Moskowitz et al. | |
| 2016/0374830 A1 | 12/2016 | Moskowitz et al. | |
| 2017/0252178 A1 | 9/2017 | Moskowitz et al. | |

OTHER PUBLICATIONS

Smith and Wendlandt, "Creating a Stewart platform model using SimMechanics," MATLAB Digest, 2002, 10(5), retrieved from URL <https://www.mathworks.com/company/newsletters/articles/creating-a-stewart-platform-model-using-simmechanics.html>.

Stewart, "A Platform with Six Degrees of Freedom," Proceedings of The Institute of Mechanical Engineers, 1965, 180: 371-386.

Analog Devices, Inc., "Small, low power, ±3-Axis 3 g iMEMS accelerometer,"ADXL330 Specifications ADXL 330, 2006, 16 pages.

(56) References Cited

OTHER PUBLICATIONS

Sensors and Signal Conditioning, 2nd Ed., John Wiley & Sons, NY, 2001, 3 pages.

* cited by examiner

ELECTRONICALLY ASSISTED MEDICAL DEVICE

The present application is a Continuation of U.S. patent application Ser. No. 16/134,364, filed Sep. 18, 2018, which is a Continuation of U.S. patent application Ser. No. 15/350,352, filed Nov. 14, 2016, now U.S. Pat. No. 10,123,881, issued on Nov. 13, 2018, which is a Continuation of U.S. patent application Ser. No. 12/945,835, filed on Nov. 13, 2010, now U.S. Pat. No. 9,492,282, issued on Nov. 15, 2016, which is a Divisional of U.S. patent application Ser. No. 11/737,846, filed on Apr. 20, 2007, now U.S. Pat. No. 7,854,765, issued on Dec. 21, 2010, which claims priority under 35 U.S.C. § 119(e) to U.S. provisional application No. 60/793,329, filed on Apr. 20, 2006, the entire contents of all the above identified patent applications are hereby incorporated by reference.

BACKGROUND OF INVENTION

1. Field of the Invention

The present invention relates to surgically implantable artificial discs and more specifically to electro-mechanical intervertebral discs ("EMDs").

2. Description of the Relevant Art

Spinal pain secondary to degenerative disc disease is a major source of disability. When conservative medical treatment fails to ameliorate disabling symptoms, a variety of surgical solutions are available. These solutions include percutaneous or open surgical discectomies, fusions and more recently, placement of prosthetic discs. Typically these treatments lead to either rigid or semi constrained motion of the disc space.

The history of artificial disc embodiments and their surgical applications in the entire spine has been thoroughly reviewed in our issued U.S. Pat. No. 7,083,650 and our two pending patent application Ser. No. 11/684,787 and Ser. No. 11/536,815 which are incorporated herein by reference. The history of spinal fusion embodiments and their surgical applications in the entire spine is thoroughly reviewed in our issued patent and pending patent applications.

Currently no available prosthetic spinal disc truly simulates natural disc function in that there are more or less static responses of the implant to changing axial loading forces. The young healthy hydrated natural disc with its viscoelastic nucleus pulposus has the natural ability to sense linear and angular degrees of motion and respond by changing volumetric shape due to different axial loading forces. Upon dehydration the capacity for dynamic expansion is lost. This amongst other changes may lead to pain generation.

Current embodiments of artificial discs have different degrees of success by replacing and expanding disc heights in a static non-dynamic manner. There are currently no known implantable systems which can constantly sense movements and dynamically respond to the entire spectrum of continuous and variable kinematic and gravitational forces, and effect a motor response by modulating natural or artificial disc volume/height.

A recent published U.S. Patent Application 20050273170, by Navarro et al., describes the incorporation of a microprocessor into an artificial disc. This microprocessor stores information which enables surgeons to moderate patients' activities during the post operative period after implantation of an artificial disc. This device, however, does not have the capabilities of dynamically responding to real time sensory information which can be transmitted real-time to screw motors and hence constantly modulate disc height, volume, angle and degrees of motion via highly tuned motor outputs in response to sensory inputs. Furthermore this device is not based on linear activation systems or rotary motor actuators.

U.S. Patent Publication 20040177531, entitled "Intelligent footwear systems", by DiBenedetto et. al., describes an intelligent system for articles of footwear that adjust automatically in response to measured performance characteristics utilizing sensors and motors. This type of modulatory system has hitherto not been incorporated into any artificial disc or joint.

In our previous patent applications identified above, we presented multiple embodiments of safely implantable spinal artificial discs. In the present application, we disclose an advance to our prior patented designs, and this advance is intended to treat and restore early and late degenerative discs by implanting an intelligent system which can dynamically sense, respond and regulate disc motion. This more closely simulates natural disc function, and thereby has the capacity to further improve the quality of life of patients with painful degenerative disc disease.

SUMMARY OF THE INVENTION

A surgically implantable artificial disc and a method for implanting such a disc are disclosed. More specifically, various electro-mechanical intervertebral discs (EMDs) are disclosed. The first two embodiments are based on linear actuation systems (LASs) comprised of axially oriented telescoping cylinders coupled with position and motion sensors that feed-back via a microchip to an internalized lead screw motor, thereby dynamically altering the height and angle of the intervertebral disc. The third and fourth embodiments employ rotary motors to actuate flexion, extension, rotation and lateral bending. These electronically controlled artificial intervertebral discs (ECAIDs) respond with great sensitivity to the full spectrum of human locomotor activities, and to 360 degrees of spinal motion. This leads to exquisitely modified dynamic disc motion in response to differing spinal positions and locomotor activity thereby accurately simulating natural spinal disc function.

BRIEF DESCRIPTION OF DRAWINGS

FIGS. 3A (1)-(4) illustrates the LAS components of the electro-mechanical artificial disc (Embodiment I).

DESCRIPTION OF THE PREFERRED EMBODIMENTS

The Medical Device

Figure 1:
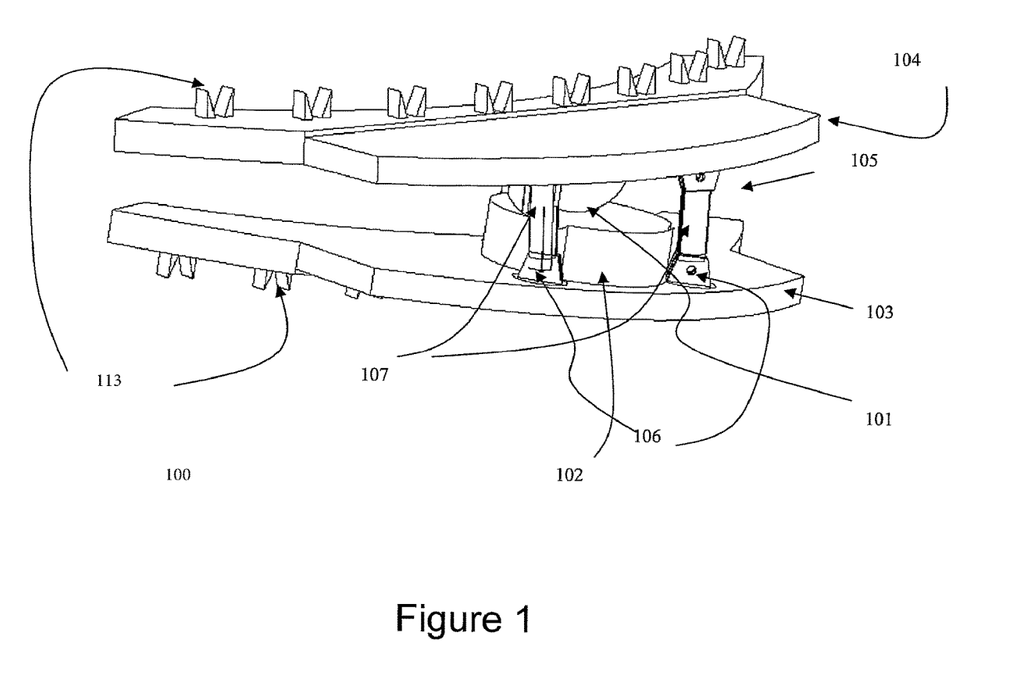
FIG. 1 illustrates an electronically assisted artificial disc with a ball/trough design, microchip, and three linear activation systems ("LASs") (Embodiment I).
Figures 3A, 3B:
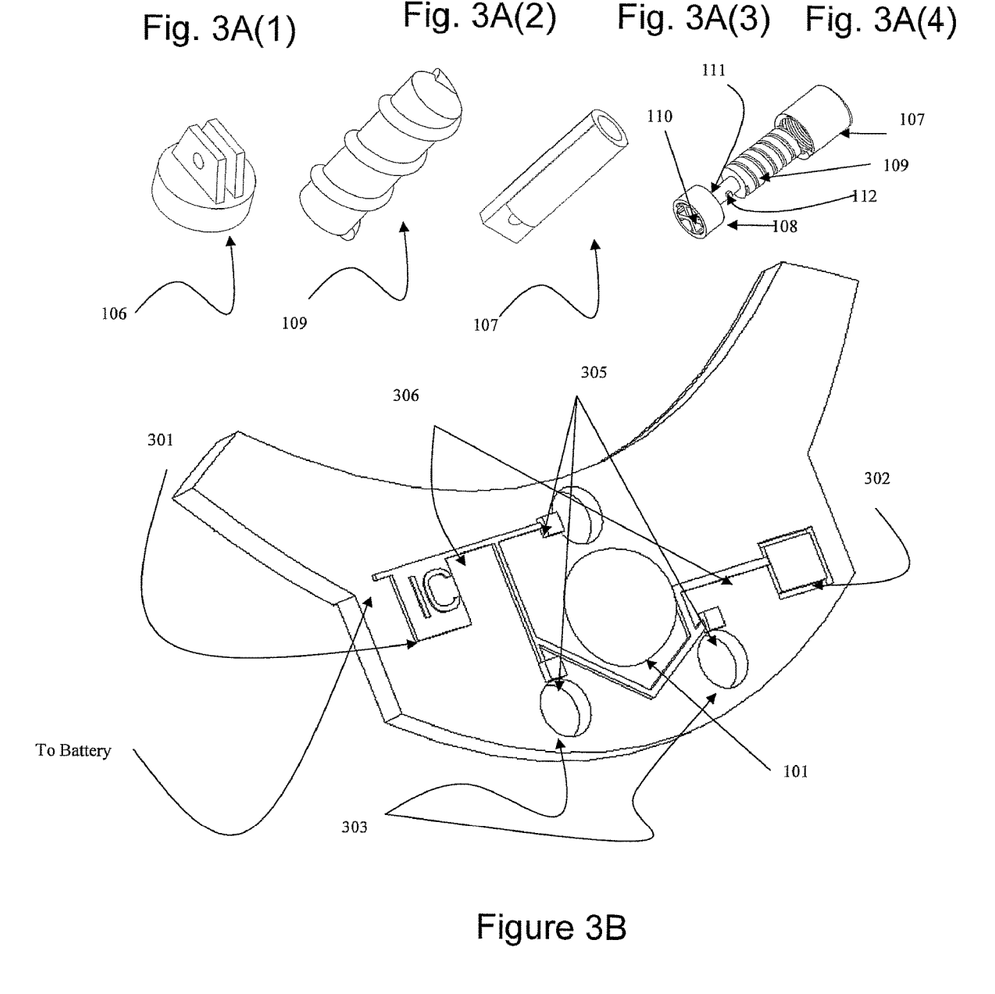
FIG. 3B illustrates the inner aspect of the EMD superior plate (Embodiment I).
Figure 3C:
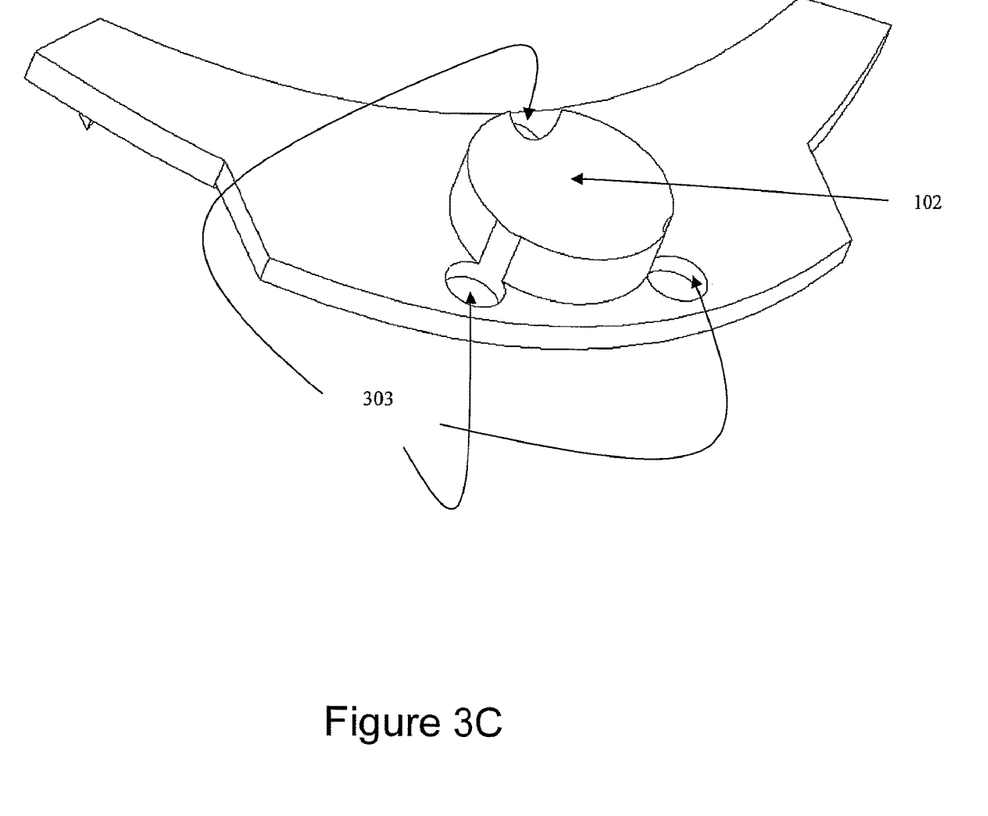
FIG. 3C illustrates the inner aspect of the EMD inferior plate (Embodiment I).

Referring now to FIGS. 1-3 the above described problem can be solved by the surgical implantation of an artificial intervertebral disc 100 having ball 101 and trough 102, with three LASs 105 placed circumferentially around the core ball/trough. The LASs 105 are each comprised of two universal joints 106, two struts 107 surrounding a motor-controlled lead screw 109 (FIGS. 1A and 3A). The motor assembly 108 for the lead-screw 109 in the LAS 105 is illustrated in FIG. 3A(4). This figure also illustrates how rotation within the motor assembly 108 effects linear motion in the struts 107. The stator 111 causes rotations in the rotor 110 thereby rotating the lead screw 109 which then causes the strut 107 to engage or disengage. In order to assess the degree of engagement or disengagement of the strut 107 from the lead screw 109 a rotation sensor 112 signals the number of turns completed by the lead screw 109. This data is processed to calculate the total change in height of the strut motor system. FIG. 3B illustrates the inner aspect of the artificial disc shell. It illustrates the hermetically sealed control circuit (microchip) 301, the gyroscopic sensor 302, slots 303 for the universal joints 106, position sensors 305 and electrical conduits 306. FIG. 3C illustrates the inner aspect of the opposing artificial disc plate 103 comprised of the trough 102 and slots 303 for the universal joints 106.

Figure 2:
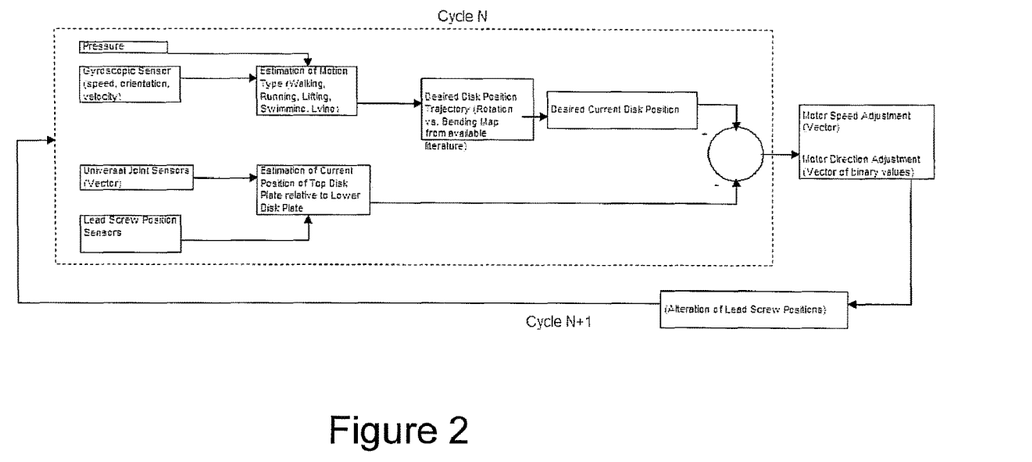
FIG. 2 illustrates a control algorithm of the electro-mechanical artificial disc (Embodiments I, II, and II).

FIG. 2 illustrates the control algorithm of the electromechanical artificial disc as it cycles. The gyroscopic sensor 302 obtains macroscopic (i.e. full body) speed, orientation and velocity. Such a gyroscopic sensor may be of a type described in ADXL330 Specifications, "Small, low power, 3-Axis ±3 g iMEMS accelerometer" ADXL330, Analog Devices, Inc., Norwood Mass., 2006. This in turn estimates motion e.g. walking, running, lifting, swimming etc. and is mapped as described in V. Feipel, T. De Mesmaeker, P. Klein, M. Rooze, "Three-dimensional kinematics of the lumbar spine during treadmill walking at different speeds", Eur. Spine J 10: 16-22, 2001, in order to find a desired position/trajectory of the disc plates. The universal joint 106 and lead screw sensors 305 obtain positions of the opposing plates 103, 104 relative to each other. The lead screw sensors 305 may be of a type described in R. Pallas-Areny, J. G. Webster, Sensors and Signal Conditioning, $2^{nd}$ Ed., John Wiley & Sons, N Y, 2001. This data is compared with a desired position/trajectory in the microchip 301, and future position of the top-plate 102 is thereby determined from the difference between current and desired positions. The lead screws 109 are then correspondingly adjusted to obtain this desired position in the LAS 105. The subsequent cycle (N+1) repeats ad infinitum at a frequency that supersedes, and is relatively much higher than, the change of macroscopic motion in the spine. The battery which can be replaceable or rechargeable is implanted percutaneously under the skin where it is easily accessible. It is also hermetically sealed.

Figure 4:
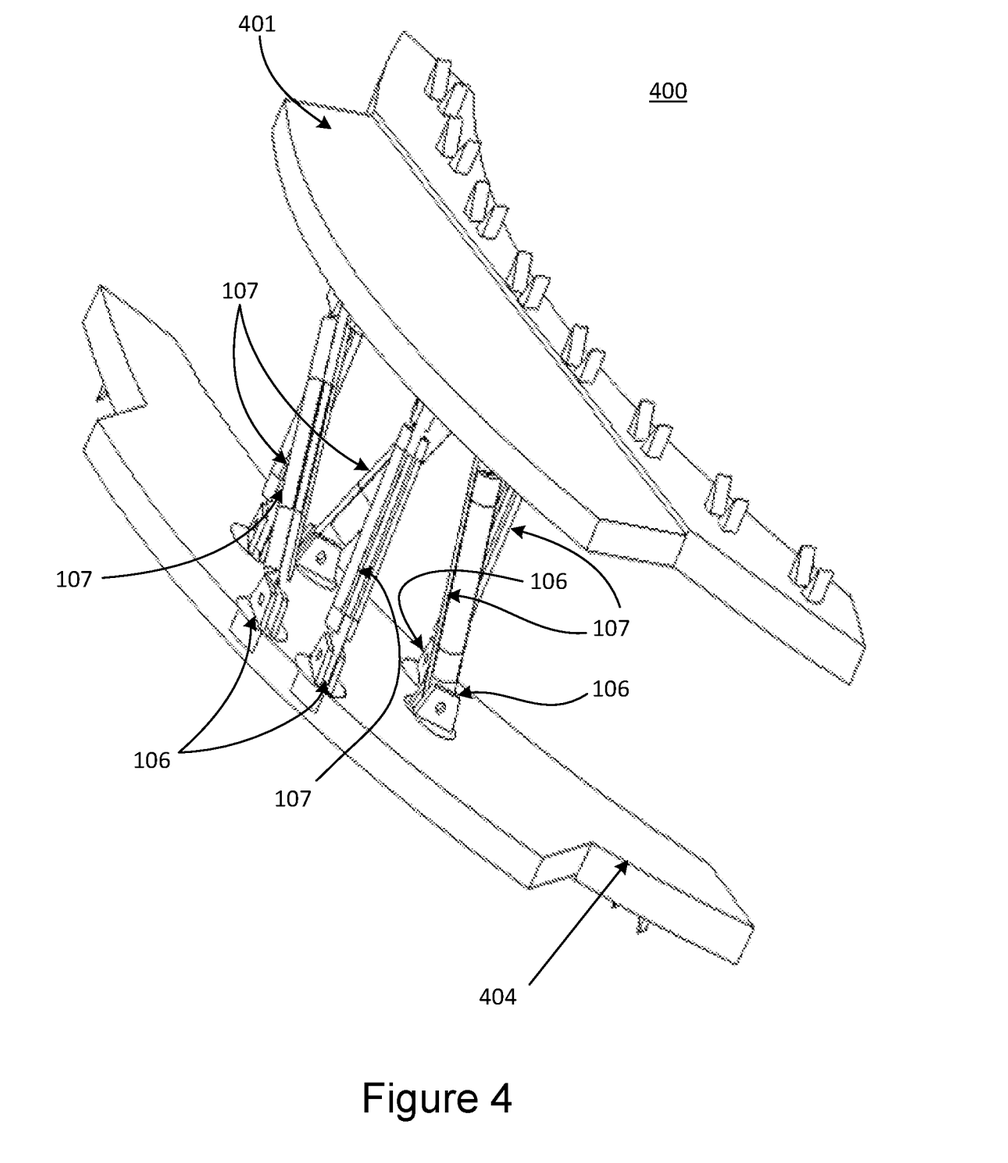
FIG. 4 illustrates a three-dimensional view of an EMD (Embodiment II).
Figure 5A:
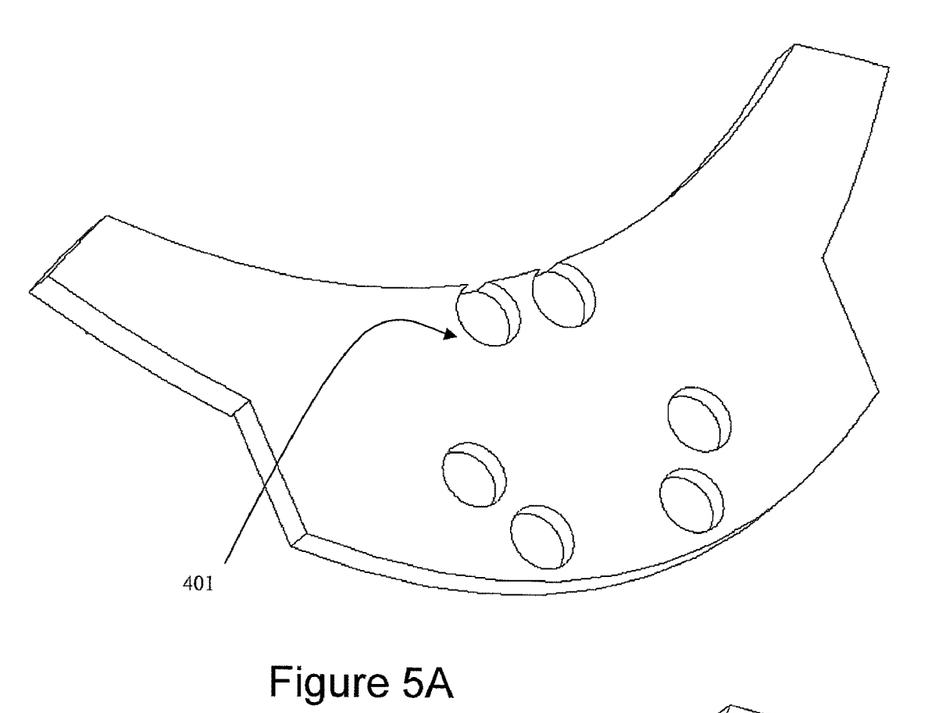
FIG. 5A illustrates the superior disc plate of the EMD (Embodiment II)
Figure 5B:
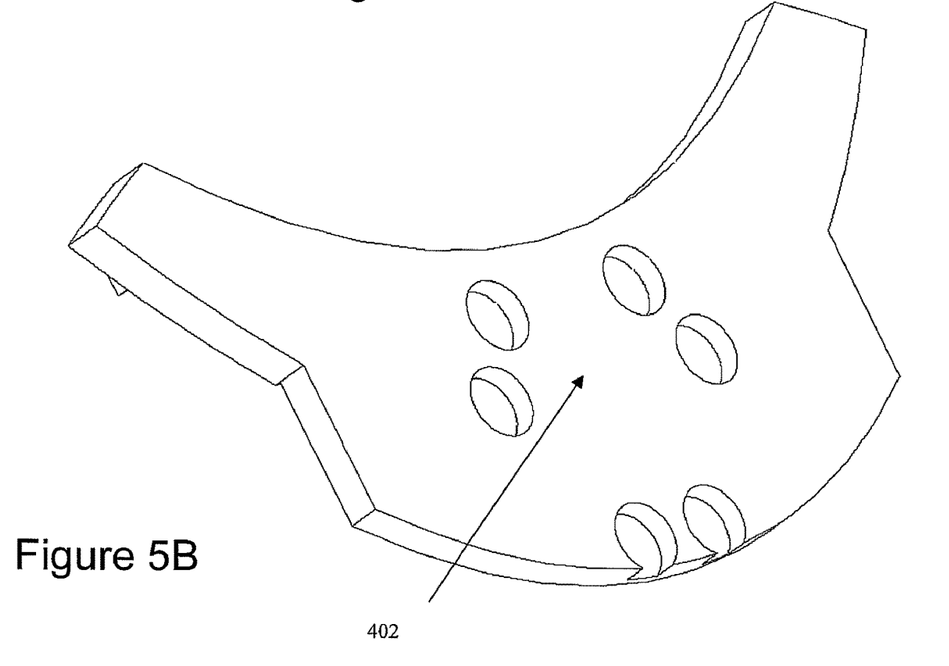
FIG. 5B illustrates the inferior disc plate of the EMD (Embodiment II).

FIG. 4 illustrates a complete electronically controlled disc 400 having plates 401 and 402 (Embodiment II). This does not have a ball and trough. Instead it has six LASs 105 that form a Stewart-type platform of the type described in N. Smith and J. Wendlandt, "Creating a Stewart platform model using SimMechanics", Newsletter—MATLAB Digest, The MathWorks, Inc, Natick Mass., September 2002. See also D. Stewart, "A platform with six degrees of freedom" Proceedings of The Institution of Mechanical Engineers, 180 Part 1, No. 15, pp. 371-386, 1965-66. The structure and function of the LASs 105 is identical to Embodiment I. FIGS. 5A and 5B illustrate the LAS slot configurations for the opposing artificial disc plates 401, 402.

Figure 6A:
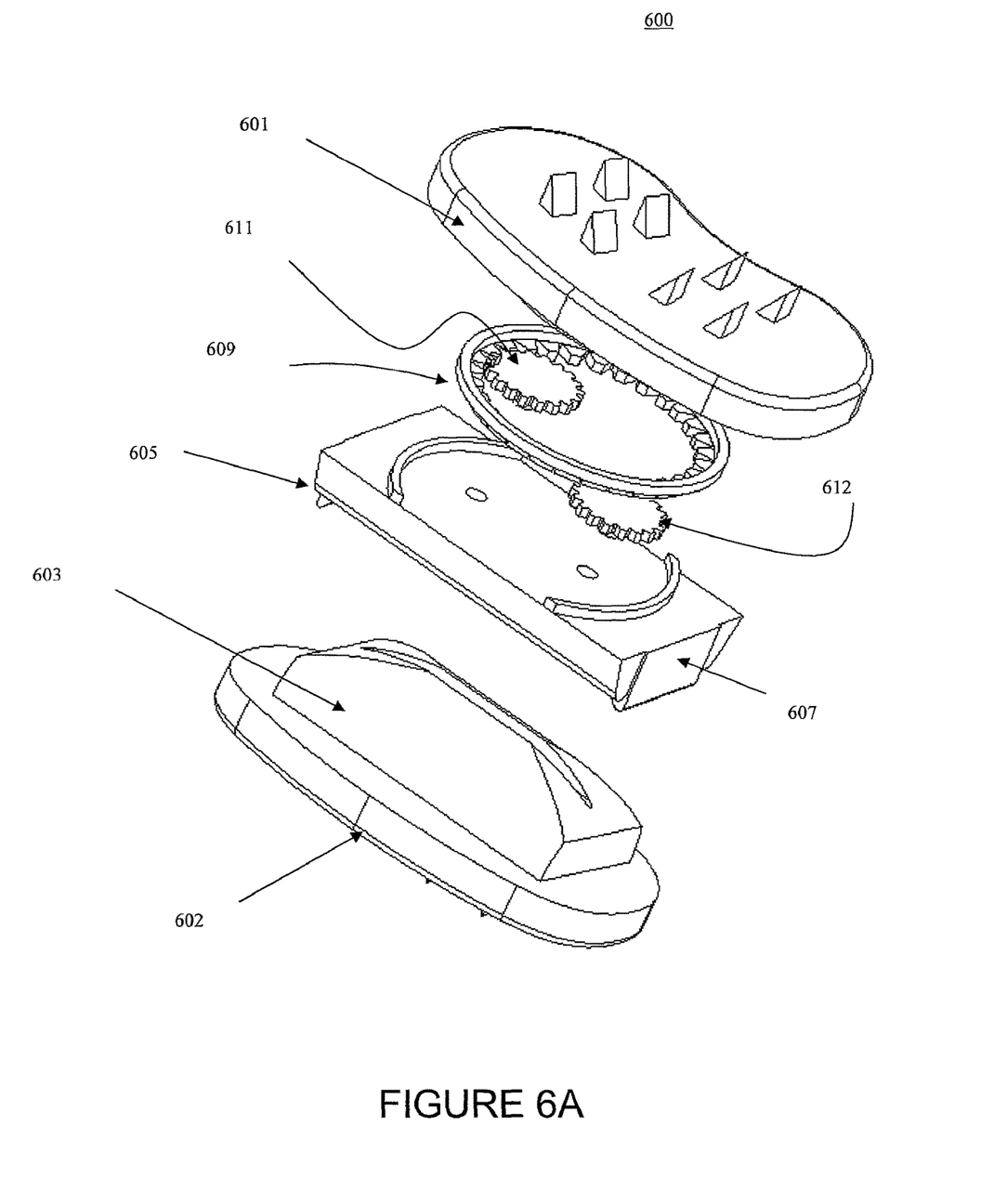
FIG. 6A illustrates an exploded view of the EMD, Roller-Bearing design (Embodiment III).
Figure 6B:
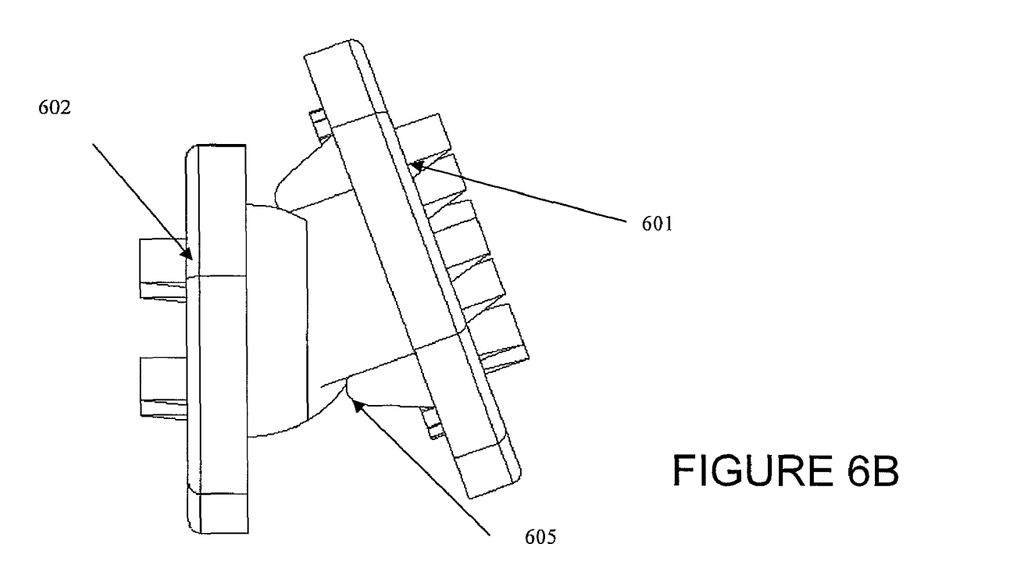
FIG. 6B illustrates a lateral view of the EMD, Roller-Bearing design (Embodiment III).
Figure 6C:
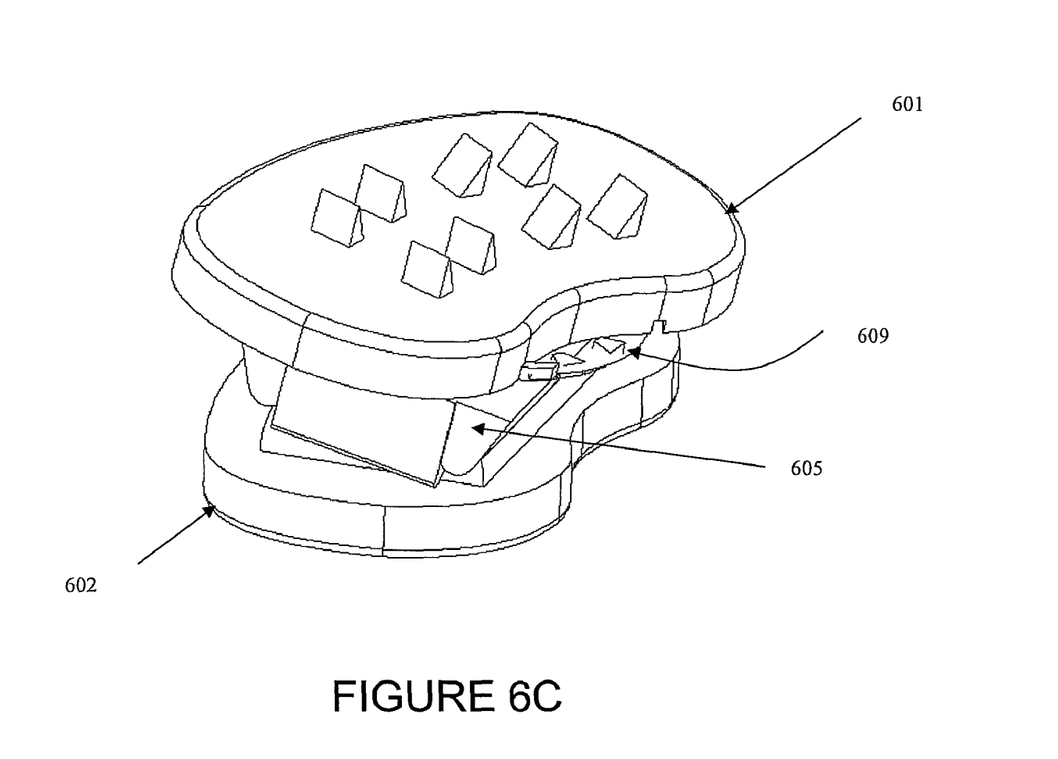
FIG. 6C illustrates a perspective view of the EMD, Roller-Bearing design (Embodiment III).

FIGS. 6 and 7 illustrate the electromechanical disc (EMD) 600, Roller-Bearing design (Embodiment III). We will now describe the mechanism of sensory-motor coupling and actuation for the EMD 600, Embodiment III. This EMD 600 has superior and inferior plates 601, 602 which are each uniquely designed (FIGS. 6A-C, and FIGS. 7A-7E). The inferior plate 602 provides motor housing 603 and a flexion/extension rotation motor shaft bearing 701 (FIG. 7E) for the shaft 620 of the roller 605 (FIG. 7D), and also has embedded motor and torque sensors 607 which sense the force with which the roller 605 rotates against the inferior plate 602 (FIGS. 6A-C). Additionally it can sense the position that the roller 605 is in.

Figure 7A:
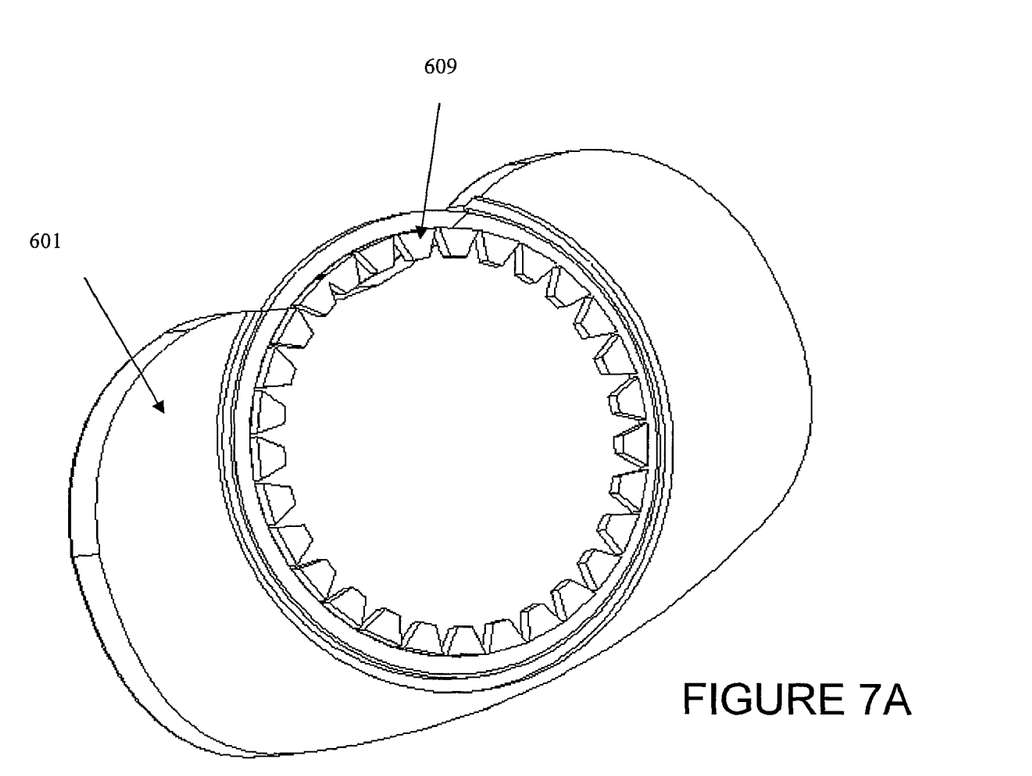
FIG. 7A illustrates the inferior aspect of the superior plate with guidance ring of EMD, Roller-Bearing design (Embodiment III).
Figure 7B:
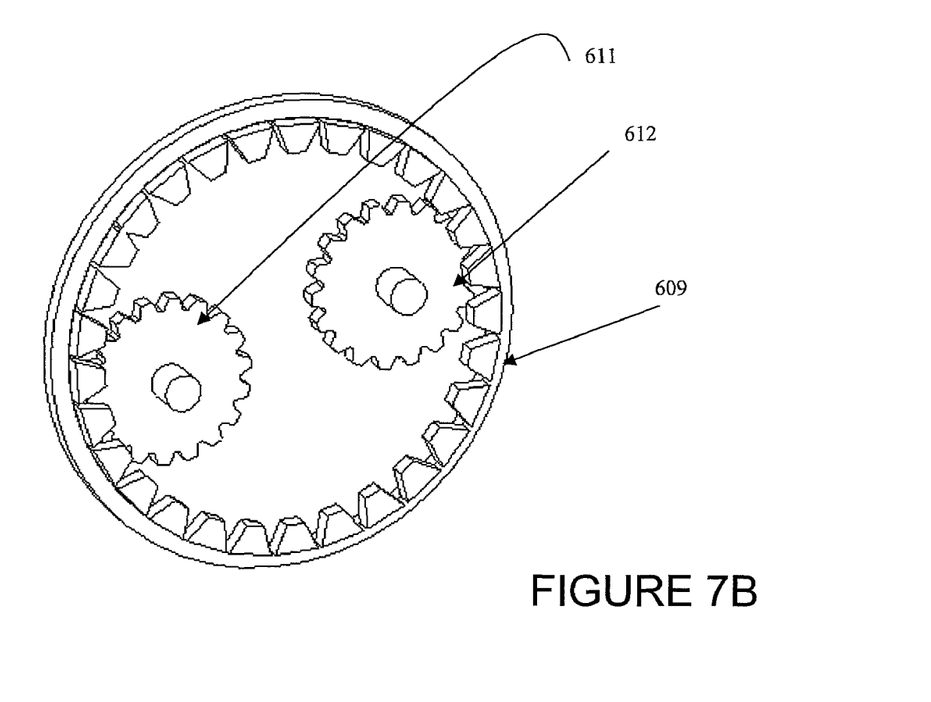
FIG. 7B illustrates the intermeshing of the guidance ring with gear motors of the EMD, Roller-Bearing design (Embodiment III).

The inferior plate 602 magnetically controls the shaft 620 and hence position of the roller 605. The position of the roller 605 determines the degree of flexion and extension exhibited by the patient.

Within the roller 605 are embedded motor and sensor 607 pair responding to spatial rotation (FIG. 6A). The sensor 607 detects the rotational position of the superior plate 601, and detects the velocity of the patient. Subsequent to this information being processed, the adjacent motor is activated initiating further rotation consistent with the predicted or anticipated motion of the superior and inferior vertebral bodies. A regenerative energy conserving power source can be incorporated into the roller 605.

The gear mesh which consists of the guidance ring 609 with two geared motors 611, 612, one of which behaves as a sensor, (FIGS. 6A, 7A and 7B) is responsible for a vertebral rotation feed-back loop. The guidance ring 609 is fixed in the superior plate 601, (FIG. 7A) therefore rotation of the superior vertebral body precisely determines the rotation of the guidance ring 609. The guidance ring 609 thereby effects a gear motor that is acting as a sensor in its passive state (FIG. 7B). Within milliseconds the other gear motor initiates a proportionate rotation, thereby rotating the guidance ring 609, and the upper vertebral body.

Figure 7C:
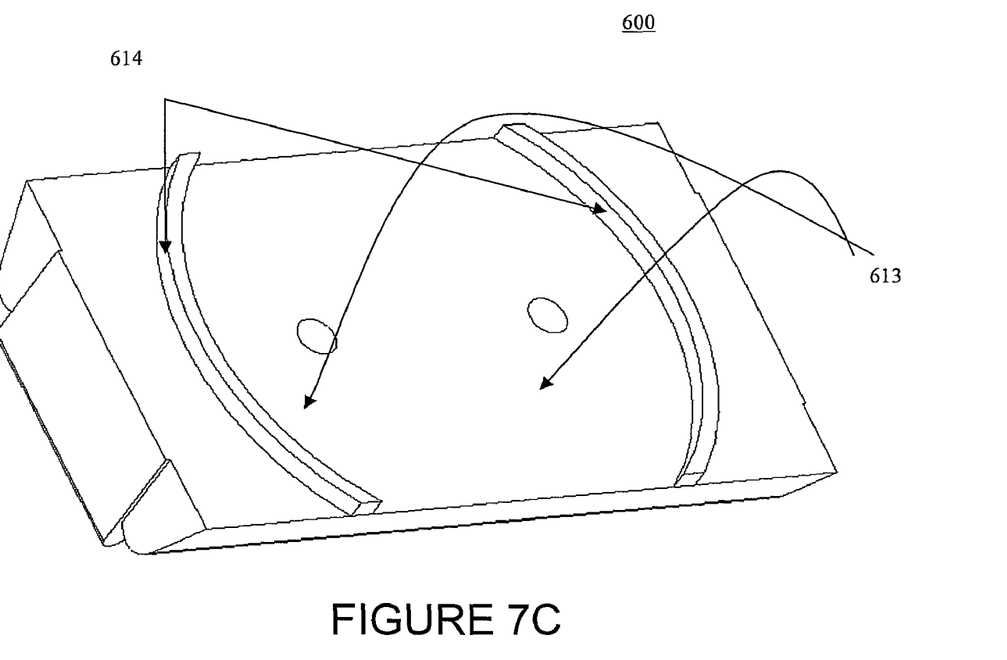
FIG. 7C illustrates the superior view of the Roller found in the EMD (Embodiment III).
Figure 7D:
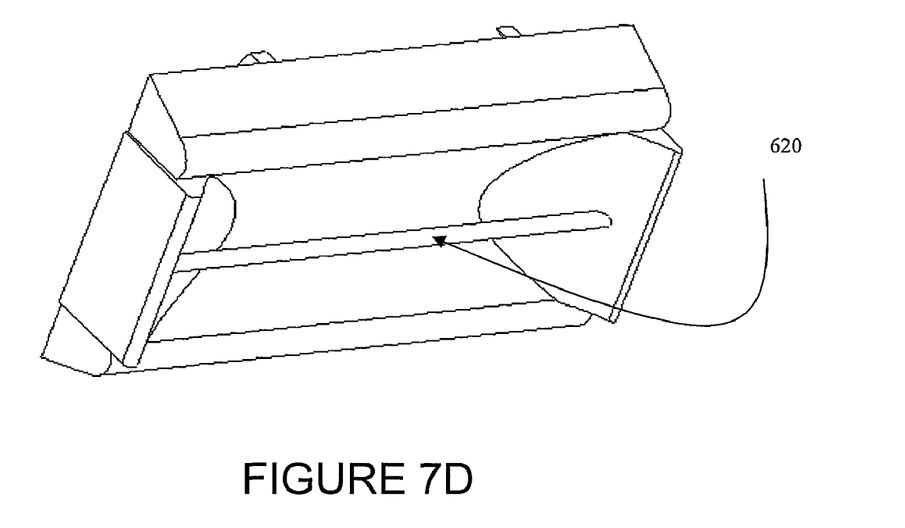
FIG. 7D illustrates the inferior view of the Roller found in the EMD (Embodiment III).
Figure 7E:
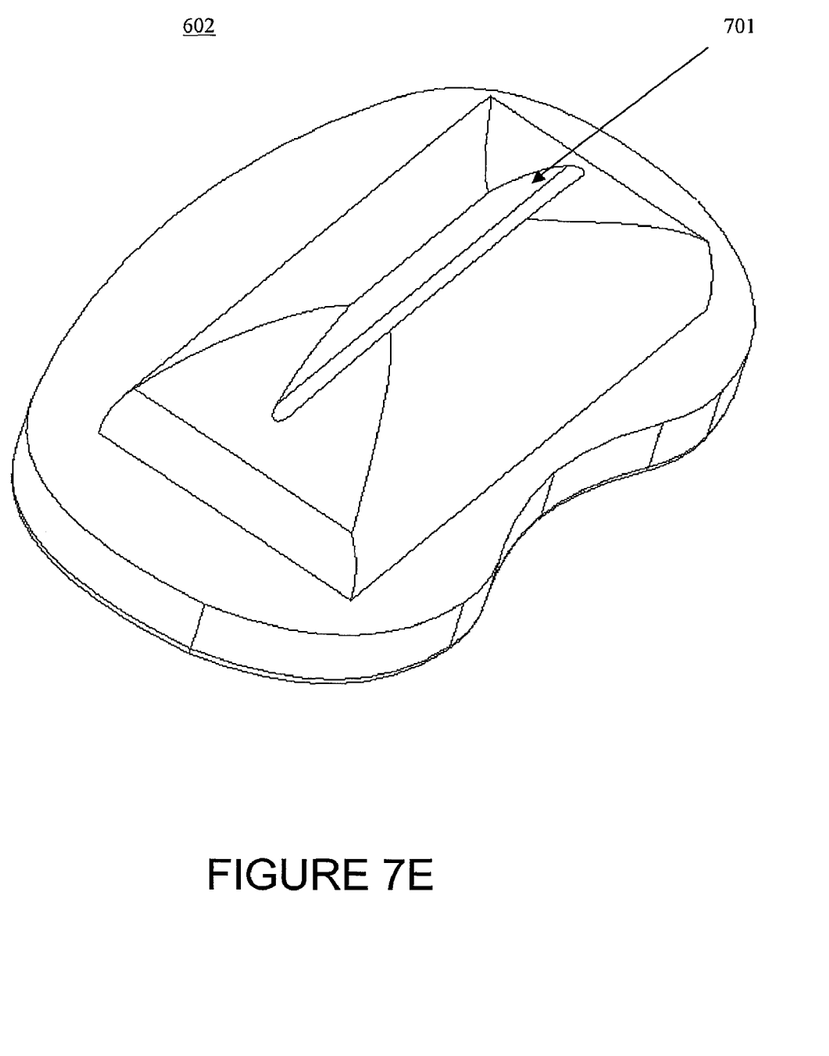
FIG. 7E illustrates the superior view of the inferior plate of the EMD (Embodiment III).

FIG. 7C illustrates that the shaft of the geared motors 611, 612 is inserted into the motor gear interface 613. The guidance ring bearings 614 serve as a bearing for the guidance ring 609.

Figure 8:
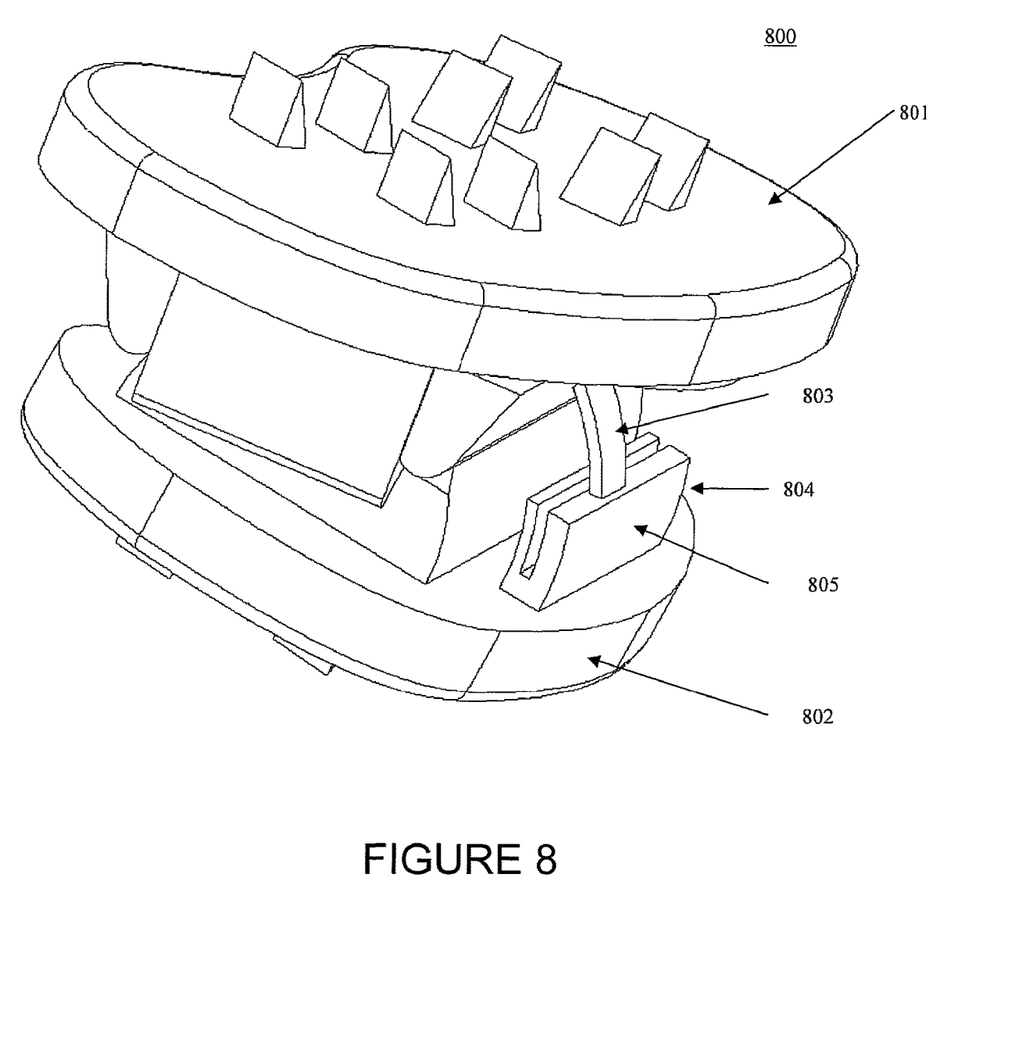
FIG. 8 illustrates a three-dimensional view of an Electromechanical Disc (EMD), Roller-Bearing design with a position-force sensor (Embodiment IV).

FIG. 8 illustrates a fourth EMD embodiment 800 which is based on a Roller-Bearing design as in Embodiment III. However, in addition to Embodiment III, it also contains a position and force sensor system 804. In Embodiment IV the superior disc plate 801 is rigidly attached to a curved protruding element 803. Correspondingly the inferior disc plate 802 is rigidly attached to a curved slot element 805. The protruding element 803 has the ability to rotate within the slot element 805 as well as to translate along the slot element 805. The slot element 805 will sense the acceleration and position of the protruding element 803, and thereby obtain the force and position experienced by the superior and inferior disc plates 801, 802.

Surgical Approach

The surgical implantation of embodiments I, II, III and IV is identical to the techniques described in our previous patent and patent applications, U.S. Pat. No. 7,083,650 and pending patent application Ser. No. 11/684,787 and Ser. No. 11/536,815. In addition, after implantation, the insulated leads are brought to the dorsal surface, attached to the comptroller power complex which is buried subcutaneously allowing battery access (not illustrated).

The current embodiments for placement of ECAIDs further enhance prosthetic disc function by more closely simulating the natural disc function by dynamically responding to changes in locomotion and spinal motion gradients hence making it a more effective disc substitute which provides constant real-time dynamic changes.

These embodiments have the potential to lead to significant advances in the care of the spinal patient. Furthermore it is possible that this technology in the future may be applicable to other early diseased joints in the body.

The invention has been described with reference to exemplary embodiments. However, it will be readily apparent to those skilled in the art that it is possible to embody the invention in specific forms other than those of the embodiments described above. This may be done without departing from the sprit of the invention. The exemplary embodiments are merely illustrative and should not be considered restrictive in any way. The scope of the invention is given by the appended claims, rather than the preceding description, and all variations and equivalents which fall within the range of the claims are intended to be embraced therein.

We claim:

1. An electronically assisted artificial vertebral disc, comprising:
    an upper disc plate;
    a lower disc plate disposed beneath the upper disc plate;
    an actuator for imparting movement to at least one of the upper and lower disc plates;
    a control device for controlling the actuator and an amount of movement between the disc plates;
    a bearing support surface disposed on a first plate of the upper disc plate and the lower disc plate; and
    a roller and shaft disposed on a second plate of the upper disc plate and the lower disc plate, the roller and the shaft rotatably cooperating with the bearing support surface on the first plate;
    wherein the actuator includes a first motor disposed on the first plate and configured to rotate the shaft, and a second motor disposed on the second plate and configured to rotate the roller; and
    wherein a position of the shaft is magnetically controlled by the first plate.

2. The electronically assisted artificial vertebral disc according to claim 1 wherein the roller is operatively coupled to a guidance ring which is fixed to the disc plate supporting the roller, said guidance ring guiding at least two gears, one of the gears being coupled to the second motor and the other gear being responsive to the rotation of the roller relative to its support disc plate.

3. The electronically assisted artificial vertebral disc according to claim 2, wherein the control device includes,
    at least a first sensor for detecting rotation of the shaft with respect to the bearing surface;
    at least a second sensor for detecting a torque exerted on the roller;
    at least a third sensor for detecting a spatial orientation of at least one of the upper and lower disc plates; and
    a microprocessor that calculates desired positions of the upper and lower disc plates and provides control signals to the first and second motors to drive the upper and lower disc plates to their desired positions.

4. The electronically assisted artificial vertebral disc according to claim 3, wherein the third sensor includes a gyroscopic sensor.

5. The electronically assisted artificial vertebral disc according to claim 2, wherein the control device includes,
    at least a first sensor for detecting a position of the shaft with respect to the bearing surface and a force experienced by the upper and lower disc plates;
    at least a second sensor for detecting a spatial orientation of at least one of the upper and lower disc plates; and
    a microprocessor that calculates desired positions of the upper and lower disc plates and provides control signals to the first and second motors to drive the upper and lower disc plates to their desired positions.

6. The electronically assisted artificial vertebral disc according to claim 5, wherein the first sensor includes a protruding curved element and a slot element that permits translation and rotation of the curved element.

7. The electronically assisted artificial vertebral disc according to claim 1, wherein the upper disc plate and the lower disc plate each has a flat vertebral body-facing surface.

8. The electronically assisted artificial vertebral disc according to claim 1, wherein the first plate magnetically controls the position of the shaft to determine a degree of flexion and extension by the electronically assisted artificial vertebral disc.

* * * * *